US011873268B2

(12) United States Patent
Symreng et al.

(10) Patent No.: US 11,873,268 B2
(45) Date of Patent: Jan. 16, 2024

(54) PROCESS FOR THE PRODUCTION OF UREA FORMALDEHYDE CONCENTRATE

(71) Applicant: Haldor Topsøe A/S, Kgs. Lyngby (DK)

(72) Inventors: Marcus Symreng, Malmö (SE); Pat A. Han, Smørum (DK)

(73) Assignee: Topsoe A/S, Kgs. Lyngby (DK)

( * ) Notice: Subject to any disclaimer, the term of this patent is extended or adjusted under 35 U.S.C. 154(b) by 267 days.

(21) Appl. No.: 17/420,025

(22) PCT Filed: Mar. 5, 2020

(86) PCT No.: PCT/EP2020/055861
§ 371 (c)(1),
(2) Date: Jun. 30, 2021

(87) PCT Pub. No.: WO2020/187583
PCT Pub. Date: Sep. 24, 2020

(65) Prior Publication Data
US 2022/0048853 A1 Feb. 17, 2022

(30) Foreign Application Priority Data
Mar. 15, 2019 (DK) .......................... PA 2019 00321

(51) Int. Cl.
C07C 273/04 (2006.01)
C07C 29/152 (2006.01)
C07C 273/10 (2006.01)
C07C 45/38 (2006.01)
C07C 29/151 (2006.01)
C01C 1/04 (2006.01)
C01B 3/38 (2006.01)
C01B 3/02 (2006.01)

(52) U.S. Cl.
CPC ............ *C07C 273/04* (2013.01); *C01B 3/025* (2013.01); *C01B 3/382* (2013.01); *C01C 1/0488* (2013.01); *C07C 29/152* (2013.01); *C07C 29/1518* (2013.01); *C07C 45/38* (2013.01); *C07C 273/10* (2013.01); *C01B 2203/0233* (2013.01); *C01B 2203/0244* (2013.01); *C01B 2203/0288* (2013.01); *C01B 2203/0415* (2013.01); *C01B 2203/0445* (2013.01); *C01B 2203/0475* (2013.01); *C01B 2203/061* (2013.01); *C01B 2203/068* (2013.01)

(58) Field of Classification Search
None
See application file for complete search history.

(56) References Cited

U.S. PATENT DOCUMENTS

2007/0299144 A1 12/2007 Davey et al.
2019/0031604 A1 1/2019 Erlandsson et al.

FOREIGN PATENT DOCUMENTS

| EP | 1230203 B1 | 2/2004 | |
|---|---|---|---|
| GB | 2231040 A | 11/1990 | |
| WO | WO-2018078318 A1 * | 5/2018 | ............... C01B 3/02 |
| WO | WO 2018/166873 A1 | 9/2018 | |

* cited by examiner

Primary Examiner — Amy C Bonaparte
(74) Attorney, Agent, or Firm — Blank Rome LLP

(57) ABSTRACT

Parallel co-production process for the production of methanol and urea product from a hydrocarbon containing feedstock by means of primary and secondary reforming, intermediary methanol and ammonia formation and conversion of the ammonia to urea product and catalytic oxidation of methanol to formaldehyde.

3 Claims, No Drawings

PROCESS FOR THE PRODUCTION OF UREA FORMALDEHYDE CONCENTRATE

The present invention relates to a process for the production of urea formaldehyde concentrate from a hydrocarbon feed feedstock.

More particularly the invention is concerned with a parallel co-production process for the production of methanol and urea product from a hydrocarbon containing feedstock by means of primary and secondary reforming, intermediary methanol and ammonia formation and conversion of the ammonia to urea product and catalytic oxidation of methanol to formaldehyde.

Production of urea by conversion of ammonia and carbon dioxide is a well-known process and conventionally employed in the industry.

It is the general object of the invention to provide a cost effective, simple and robust process for the production of urea formaldehyde concentrate in a unit that requires a minimum of equipment and unit operations.

Accordingly, the invention provides a process for the production of urea formaldehyde concentrate from a hydrocarbon feedstock comprising steps of:

(a) producing a synthesis gas containing hydrogen, carbon monoxide and dioxide and nitrogen by steam reforming the hydrocarbon feedstock in a primary reforming stage and subsequently in a secondary reforming stage;

(b) splitting the synthesis gas from step (a) into a methanol synthesis gas and an ammonia synthesis gas;

(c) subjecting the ammonia synthesis gas from step (b) in series to a high temperature water gas shift and a low temperature water gas shift conversion;

(d) removing at least part of the carbon dioxide from the ammonia synthesis gas from step (c) to obtain a carbon dioxide depleted ammonia synthesis gas;

(e) subjecting a carbon dioxide depleted ammonia synthesis gas from step (d) to catalytic methanation to remove the unconverted carbon monoxide to obtain a purified ammonia synthesis gas;

(f) catalytically converting the nitrogen and hydrogen in the purified ammonia synthesis gas from step (e) in an ammonia synthesis stage and withdrawing an effluent containing ammonia; and (g) passing at least part of the ammonia containing effluent to an urea synthesis stage and converting the ammonia in the effluent to urea product by reaction with at least part of the carbon dioxide being removed from the synthesis gas in step (d), (h) catalytically converting the carbon monoxide, carbon dioxide and hydrogen of the methanol synthesis gas from step (b) in a once-through methanol synthesis stage and withdrawing an effluent containing methanol and an effluent containing nitrogen, hydrogen and unconverted carbon monoxide and carbon dioxide;

(i) recycling the effluent containing nitrogen, hydrogen and un-converted carbon monoxide and carbon dioxide to a fuel header as fuel to the primary reforming stage in step (a) and/or to the low temperature shift conversion in step (c);

(j) subjecting the effluent containing methanol to distillation and withdrawing purified methanol from the distillation;

(k) oxidizing at least a part of the purified methanol from step (j) to formaldehyde;

(l) absorbing the formaldehyde from step (k) in an absorber with water and an aqueous urea solution prepared from the urea product in step (g) to obtain the urea formaldehyde concentrate.

In the operation of the methanol synthesis in a once-through synthesis is as mentioned above that a synthesis gas compressor is not necessary for the methanol synthesis. The benefit of avoiding compression is that is saving of CAPEX wise by not including a compressor in the methanol synthesis. It will make the process easier as there is less maintenance required and there are fewer rotating equipments that might fail and trip the plant. This is very advantageous in a small plant as a compressor would be a big part of the investment.

As used herein the term "primary reforming stage" means reforming being conducted in a conventional steam methane reformer (SMR), i.e. tubular reformer with the heat required for the endothermic reforming being provided by radiation heat from burners, such as burners arranged along the walls of the tubular reformer.

As an advantage of the process according to the invention, at least part of the fuel to the burners in the primary reforming stage is provided by the effluent containing nitrogen, hydrogen and un-converted carbon monoxide and carbon dioxide recycled from the methanol synthesis.

As also used herein the term "secondary reforming stage" means reforming being conducted in an autothermal reformer or catalytic partial oxidation reactor.

Suitable hydrocarbon feed stocks for use in the invention include methane, natural gas, LPG, naphtha and higher hydrocarbons.

Preferably, the hydrocarbon feedstock comprises methane, for instance in the form of natural gas, liquefied natural gas (LNG) or substitute natural gas (SNG).

When employing naphtha and higher hydrocarbons, it is preferred to subject these feedstocks to a prereforming step prior to the primary reforming stage. However, prereforming can be employed for all types of hydrocarbon feed stock.

The secondary reforming is conducted in a secondary reformer or autothermal reformer fed with air or oxygen enriched air in order to provide the required amount of nitrogen for the ammonia synthesis and the required amount of carbon monoxide, carbon dioxide and hydrogen for the methanol synthesis together with required amount of carbon dioxide necessary for the conversion of ammonia to urea.

Final control of the carbon monoxide/carbon dioxide ratio to meet the required amount of nitrogen, carbon monoxide, carbon dioxide and hydrogen for ammonia synthesis together with required amount of carbon dioxide necessary for the conversion of ammonia to urea, is obtained by subjecting the ammmonia synthesis gas to the high temperature and low temperature water gas shift reaction prior to the removal of carbon dioxide in step (d).

Removal of carbon dioxide from the ammonia synthesis gas may be performed by any conventional means in a physical or chemical wash as known in the art.

Preferably, carbon dioxide removal is performed by the OASE process available from BASF, which allows easy recovery of absorbed carbon dioxide for use in the urea synthesis.

The methanol synthesis stage is preferably conducted by passing the synthesis gas at moderate pressure, such as 30-60 bar and temperatures 150-300° C. through at least one methanol reactor containing at least one, but preferably two fixed beds of methanol catalyst. A particularly preferred methanol reactor is a fixed bed reactor cooled by a suitable cooling agent such as boiling water, e.g. boiling water reactor (BWR).

In step (h) the methanol rich effluent is preferably a liquid effluent. This effluent is obtained by cooling and condensation of the effluent gas from the methanol reactors.

Accordingly the process of the invention may further comprise cooling the synthesis gas withdrawn from each methanol reactor to condense methanol and passing the gas through a separator, withdrawing a bottom fraction from the separator containing the raw methanol, withdrawing an overhead fraction containing un-converted synthesis gas which is either passed to the fuel header as fuel for the primary reformer burners and/or the low temperature shift conversion for boosting the hydrogen concentration in the shifted ammonia synthesis gas.

The effluent gas is added to the LTS with the aid of an ejector, where the main flow from the HTS acts as a motive flow and the effluent the suction flow. Alternatively, the effluent is added upstream the LTS via a booster compressor/blower which increases the effluent pressure to fit the main process gas flow.

It would be understood that the term "methanol reactor" as used herein encompasses adiabatic fixed bed reactors and cooled reactors such as boiling water reactors and reactors of the condensing-methanol type which comprises within a common shell a fixed bed of methanol catalyst particles and cooling means adapted to indirectly cooling the methanol synthesis gas with a cooling agent.

In step (e) the catalytic methanation stage for conversion of carbon monoxide to methane is conducted in at least one methanation reactor, which is preferably an adiabatic reactor containing a fixed bed of methanation catalyst.

In step (f) the ammonia synthesis gas from the methanation stage containing the correct proportion of hydrogen and nitrogen ($H_2:N_2$ molar ratio of 3:1) is optionally passed through a compressor to obtain the required ammonia synthesis pressure, such as 120 to 250 bar, preferably about 190 bar. Ammonia is then produced in a conventional manner by means of an ammonia synthesis loop comprising at least one ammonia converter. Ammonia may be recovered from the effluent containing ammonia as liquid ammonia by condensation and subsequent separation.

In order to improve the energy efficiency of the process a purge-gas stream containing hydrogen, nitrogen, ammonia and various inerts from step (f) is sent to a recovering unit, where the hydrogen is returned to the synthesis gas compressor in step (f) and the ammonia is recovered and sent to the ammonia product stream. The cleaned purge gas is sent to the reformer fuel header where it is used as fuel in step (a), i.e. it is returned as off-gas fuel to the reforming section of the plant, specifically to the primary reforming stage.

The ammonia being withdrawn from the ammonia synthesis is then converted to the urea product by reaction with carbon dioxide recovered from step (d) as described above.

To produce the formaldehyde employed in the preparation of the urea formaldehyde concentrate, at least a part of the purified methanol withdrawn from the distillation in step (j) is sent to a formaldehyde unit (k), where the methanol is either preheated and quenched into preheated air, or evaporated and mixed with the preheated air, before it is oxidized over an oxidation catalyst to formaldehyde.

The formaldehyde produced in the methanol oxidation step (k) is subsequently passed into a formaldehyde absorber. In the formaldehyde absorber, the gaseous formaldehyde effluent from the oxidation step absorbed in water and aqueous urea suspension to form a Urea Formaldehyde Concentrate.

A major part of the effluent gas leaving the absorber top is sent back to the preheated air in (k), while the rest is preheated and catalytically incinerated in an incinerator reactor before it is purged to avoid build-up of inerts.

The invention claimed is:

1. A process for the production of a urea formaldehyde concentrate from a hydrocarbon feedstock comprising steps of:
   (a) producing a synthesis gas containing hydrogen, carbon monoxide, carbon dioxide and nitrogen by steam reforming the hydrocarbon feedstock in a primary reforming stage and subsequently in a secondary reforming stage;
   (b) splitting the synthesis gas from step (a) into a methanol synthesis gas and an ammonia synthesis gas;
   (c) subjecting the ammonia synthesis gas from step (b) in series to a high temperature water gas shift and a low temperature water gas shift conversion;
   (d) removing at least part of the carbon dioxide from the ammonia synthesis gas from step (c) to obtain a carbon dioxide depleted ammonia synthesis gas;
   (e) subjecting the carbon dioxide depleted ammonia synthesis gas from step (d) to catalytic methanation to remove the unconverted carbon monoxide to obtain a purified ammonia synthesis gas;
   (f) catalytically converting the nitrogen and hydrogen in the purified ammonia synthesis gas from step (e) in an ammonia synthesis stage and withdrawing an effluent containing ammonia;
   (g) passing at least part of the ammonia containing effluent to a urea synthesis stage, converting the ammonia in the effluent to urea product by reaction with at least part of the carbon dioxide being removed from the synthesis gas in step (d), and preparing an aqueous urea solution from the urea product;
   (h) catalytically converting the carbon monoxide, carbon dioxide and hydrogen of the methanol synthesis gas from step (b) in a once-through methanol synthesis stage and withdrawing an effluent containing methanol and an effluent containing nitrogen, hydrogen and unconverted carbon monoxide and carbon dioxide;
   (i) recycling the effluent containing nitrogen, hydrogen and un-converted carbon monoxide and carbon dioxide: (i) to a fuel header as fuel to the primary reforming stage in step (a) and/or (ii) to the low temperature shift conversion in step (c);
   (j) subjecting the effluent containing methanol to distillation and withdrawing purified methanol from the distillation;
   (k) oxidizing at least a part of the purified methanol from step (j) to formaldehyde;
   (l) absorbing the formaldehyde from step (k) in an absorber with water and the aqueous urea solution prepared from the urea product in step (g) to obtain the urea formaldehyde concentrate,
   wherein the effluent containing nitrogen, hydrogen and unconverted carbon monoxide and carbon dioxide in step (i) is recycled to the low temperature shift conversion in step (c) with an ejector using main flow from the high temperature water gas shift as motive flow and the effluent as suction flow.

2. The process of claim 1, further comprising admixing the urea formaldehyde concentrate to urea pellets or granulate.

3. The process according to claim 1, the methanol synthesis stage in step (h) is performed in at least one methanol reactor containing one or two fixed beds comprising a methanol catalyst.

* * * * *